US010626335B2

(12) United States Patent
Rogers et al.

(10) Patent No.: US 10,626,335 B2
(45) Date of Patent: *Apr. 21, 2020

(54) PROCESS FOR REMOVING METALS FROM HYDROCARBONS

(75) Inventors: Robin Don Rogers, Belfast (GB); John Holbrey, Belfast (GB); Hector Rodriguez, Belfast (GB)

(73) Assignee: Petroliam Nasional Berhad (Petronas), Kuala Lumpur (MY)

( * ) Notice: Subject to any disclaimer, the term of this patent is extended or adjusted under 35 U.S.C. 154(b) by 723 days.

This patent is subject to a terminal disclaimer.

(21) Appl. No.: 13/263,099

(22) PCT Filed: Mar. 30, 2010

(86) PCT No.: PCT/GB2010/050549
§ 371 (c)(1),
(2), (4) Date: Dec. 22, 2011

(87) PCT Pub. No.: WO2010/116165
PCT Pub. Date: Oct. 14, 2010

(65) Prior Publication Data
US 2012/0121485 A1 May 17, 2012

(30) Foreign Application Priority Data
Apr. 6, 2009 (GB) .................. 0905896.7

(51) Int. Cl.
C10G 21/27 (2006.01)
C07D 213/57 (2006.01)
C10G 25/00 (2006.01)
C07D 233/58 (2006.01)
B01D 11/04 (2006.01)

(52) U.S. Cl.
CPC .......... *C10G 21/27* (2013.01); *B01D 11/0492* (2013.01); *C07D 213/57* (2013.01); *C07D 233/58* (2013.01); *C10G 25/003* (2013.01); *C10G 2300/104* (2013.01); *C10G 2300/1025* (2013.01); *C10G 2300/1033* (2013.01); *C10G 2300/1044* (2013.01); *C10G 2300/1051* (2013.01); *C10G 2300/1055* (2013.01); *C10G 2300/205* (2013.01)

(58) Field of Classification Search
None
See application file for complete search history.

(56) References Cited

U.S. PATENT DOCUMENTS

| | | | |
|---|---|---|---|
| 4,562,511 A * | 12/1985 | Nishino ............... | H01G 9/155 361/315 |
| 4,915,818 A | 4/1990 | Yan ..................... | 208/251 R |
| 4,946,582 A | 8/1990 | Torihata et al. ....... | 208/251 R |
| 5,037,552 A | 8/1991 | Furuta et al. .......... | 210/634 |
| 5,504,138 A * | 4/1996 | Jacobs ............... | C08G 18/0885 252/511 |
| 8,871,668 B2 * | 10/2014 | Kobayashi ........... | B01J 31/0252 502/168 |
| 9,447,335 B2 * | 9/2016 | Abai ..................... | C10G 25/003 |
| 2003/0075484 A1 * | 4/2003 | Sakai ..................... | C10G 29/10 208/251 R |
| 2003/0085156 A1 | 5/2003 | Schoonover ............ | 208/230 |
| 2004/0035293 A1 * | 2/2004 | Davis, Jr. ................ | C07C 45/46 95/140 |
| 2007/0123660 A1 | 5/2007 | degouvea-Pinto et al. .. | 525/342 |
| 2010/0179311 A1 * | 7/2010 | Earle et al. .................. | 536/26.1 |
| 2011/0081286 A1 * | 4/2011 | Sasson ............... | B01D 53/1493 423/215.5 |
| 2011/0085952 A1 * | 4/2011 | Sasson ............... | B01D 53/1493 423/210 |
| 2011/0139687 A1 * | 6/2011 | Yeganeh et al. .............. | 208/253 |
| 2012/0132564 A1 * | 5/2012 | Hardacre et al. .............. | 208/14 |
| 2015/0194782 A1 * | 7/2015 | Eden ................. | H01S 3/094096 372/70 |

FOREIGN PATENT DOCUMENTS

| | | |
|---|---|---|
| CA | 2465374 | 8/2003 |
| CA | 2465374 * | 8/2005 |
| CA | 2660334 | 2/2008 |
| CN | 101240377 * | 8/2008 |
| EP | 1854786 | 11/2007 |
| EP | 1911829 | 4/2008 |
| GB | 2 418 926 | 4/2006 |
| JP | 60129125 | 7/1985 |
| JP | 3043495 | 7/1989 |
| JP | 3250092 | 2/1990 |
| JP | 2001172646 | 6/2001 |
| WO | 02/34863 | 5/2002 |
| WO | 2006/072775 | 7/2006 |
| WO | 2007/101397 | 9/2007 |

(Continued)

OTHER PUBLICATIONS

International Search Report dated Oct. 15, 2010, in Application No. PCT/GB2010/050549.
Harding assay; British Petroleum Oil International; XP002588383; abstract.
Bloom, "Analysis and stability of mercury speciation in petroleum hydrocarbons", Fresenius J. Anal. Chem., 2000, 366, 349-358.
Ji et al., "Pyrrolidinium Imides: Promising Ionic Liquids for Direct Capture of Elemental Mercury from Flue Gas", Water, Air, & Soil Pollution: Focus 2008, 8, 349-358.
Ji et al., "Room Temperature Ionic Liquids for Mercury Capture from Flue Gas", Ind. Eng. Chem. Res., 2008, 47, 8396-8400.
Liu et al., "Using Bromine Gas To Enhance Mercury Removal from Flue Gas of Coal-Fired Power Plants", Environ. Sci. Technol., 2007, 41, 1405-1412.

(Continued)

Primary Examiner — Sheng H Davis
(74) Attorney, Agent, or Firm — Ryan T. Grace; Advent, LLP

(57) ABSTRACT

This invention relates to a process for removing metals, particularly mercury, from hydrocarbon streams by use of an ionic liquid, where in the metal-containing hydrocarbon stream is contacted with an ionic liquid to produce a product hydrocarbon stream having reduced mercury content.

32 Claims, No Drawings

(56) References Cited

FOREIGN PATENT DOCUMENTS

WO    2007/138307    12/2007
WO    2009/017832    2/2009

OTHER PUBLICATIONS

Rogers et al., "Mercury (II) partitioning from aqueous solutions with a new, hydrophobic ethylene-glycol functionalized bis-imidazolium ionic liquid", Green Chem., 2003, 5, 129-135.
Prausnitz et al., "Selective Extraction of Copper, Mercury, Silver, and Palladium Ions from Water Using Hydrophobic Ionic Liquids", Ind. Eng. Chem. Res., 2008, 47, 5080-5086.
Miedaner, M. M., et al., "Solubility of metallic mercury in octane, dodecane and toluene at temperatures between 100° C. and 200° C.," Geochimica et Cosmochimica Acta, vol. 69, No. 23, 2005, pp. 5511-5516.
Visser, A., et al., "Task-specific ionic liquids for the extraction of metal ions from aqueous solutions," The Journal: Chemical Communications, Issue 1, 2001, pp. 135-136.

\* cited by examiner

PROCESS FOR REMOVING METALS FROM HYDROCARBONS

This invention relates to a process for removing metals, and particularly mercury, from hydrocarbon fluids. More specifically, the invention relates to a process wherein metals are extracted from gaseous or liquid hydrocarbons using an ionic liquid.

Liquid and gaseous hydrocarbons obtained from oil and gas fields are often contaminated with mercury. In particular, liquid and gaseous hydrocarbons obtained from oil and gas fields in and around the Netherlands, Germany, Canada, USA, Malaysia, Brunei and the UK are known to contain mercury. As reported by N. S. Bloom (Fresenius J. Anal. Chem., 2000, 366, 438-443), the mercury content of such hydrocarbons may take a variety of forms. Although elemental mercury tends to predominate, particulate mercury (i.e. mercury bound to particulate matter), organic mercury (e.g. dimethylmercury and diethylmercury) and ionic mercury (e.g. mercury dichloride) may also be found in naturally occurring hydrocarbon sources. The mercury concentration in crude oils can range from below 1 part per billion (ppb) to several thousand ppb depending on the well and location. Similarly, mercury concentrations in natural gas can range from below 1 $ng \cdot m^{-3}$ to greater than 1000 $\mu g \cdot m^{-3}$.

The presence of mercury in hydrocarbons is problematic due to its toxicity. In addition, mercury is corrosive towards hydrocarbon processing equipment, such as that used in oil and gas refineries. Mercury can react with aluminium components of hydrocarbon processing equipment to form an amalgam, which can lead to equipment failure. For example, pipeline welds, cryogenic components, aluminium heat exchangers and hydrogenation catalysts can all be damaged by hydrocarbons contaminated with mercury. This can lead to plant shutdown, with severe economic implications, or, in extreme cases, to uncontrolled loss of containment or complete plant failure, with potentially catastrophic results.

Furthermore, products with high levels of mercury contamination are considered to be of poorer quality, with the result that they command a lower price.

A number of approaches to the removal of mercury from hydrocarbons have been proposed. These include: scrubbing techniques using fixed bed columns containing sulfur, transition metal or heavy metal sulfides and iodides on an activated support; oxidation followed by complexation with sulfur-containing compounds; and oxidation followed by solvent extraction.

In addition, a limited number of approaches have been proposed for the removal of mercury from hydrocarbons using of ionic liquids.

The term "ionic liquid" as used herein refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., particularly below 100° C., around room temperature (15 to 30° C.), or even below 0° C. Ionic liquids having melting points below around 30° C. are commonly referred to as "room temperature ionic liquids" and are often derived from organic salts having nitrogen-containing heterocyclic cations, such as imidazolium and pyridinium-based cations. In room temperature ionic liquids, the structures of the cation and anion prevent the formation of an ordered crystalline structure and therefore the salt is liquid at room temperature.

Ionic liquids are most widely known as solvents. Many ionic liquids have been shown to have negligible vapour pressure, temperature stability, low flammability and recyclability. Due to the vast number of anion/cation combinations that are available it is possible to fine-tune the physical properties of the ionic liquid (e.g. melting point, density, viscosity, and miscibility with water or organic solvents) to suit the requirements of a particular application.

The combination of metal-complexing ligands and ionic liquids coated onto an inert support as adsorbants to remove mercury from coal combustion flue gases has been described in US Patent Application 2007/0123660 and by Ji et al. (*Water, Air, & Soil Pollution: Focus* 2008, 8, 349-358 and *Ind. Eng. Chem. Res.*, 2008, 47, 8396-8400).

The reactivity of halogens to mercury has been utilised in flue-gas scrubbing technologies to remove metal vapour, including mercury vapour, by high temperature reaction with either bromine or chlorine to form inorganic mercury species that are readily extracted into aqueous media (see, for example, Lui, et al., *Environ. Sci. Technol.*, 2007, 41, 1405-1412).

The partitioning of mercury ions, in the high 2+ oxidation state, into ionic liquids from water has been reported by Rogers, et al. (*Green Chem.*, 2003, 5, 129-135), who showed that dicationic anionic liquid complexants can be used to partition Hg(II) from aqueous salt and acid solutions. Prausnitz, et al. (*Ind. Eng. Chem. Res.*, 2008, 47, 5080-5086) have shown that mercuric ions partition preferentially from water to hydrophobic ionic liquids.

The present invention is based on the surprising discovery that ionic liquids can be used, as effective agents to remove mercury from liquid and gaseous hydrocarbons, without additives and without the need for chemical modification of the mercury. In particular, additional solvents and/or mercury complexing ligands are not necessary to obtain efficient partitioning of mercury from liquid and gaseous hydrocarbons into an ionic liquid, although a number of co-solvents and/or additives can be incorporated if desired. Furthermore, it has also surprisingly been found that ionic liquids can be used to remove mercury from liquid and gaseous hydrocarbons preferably at, or around, ambient temperatures.

This property of ionic liquids is not known from the prior art. In particular, the known partitioning of oxidised mercuric Hg(II) ions between highly polar water and hydrophobic ionic liquids does not suggest that mercury, whether in elemental, particulate, organic or ionic forms, as commonly found in hydrocarbons, can be extracted directly from substantially non-polar hydrocarbons into an ionic liquid.

In a first aspect, the present invention provides a process for the removal of mercury from a mercury-containing hydrocarbon fluid feed comprising the steps of:
(i) contacting the mercury-containing hydrocarbon fluid feed with an ionic liquid having the formula:

[Cat$^+$][X$^-$]

wherein:
[Cat$^+$] represents one or more cationic species, and
[X$^-$] represents one or more anionic species; and
(ii) separating from the ionic liquid a hydrocarbon fluid product having a reduced mercury content compared to the mercury-containing hydrocarbon feed.

Mercury-containing hydrocarbon fluids that can be processed according to the present invention may comprise from 1 part per billion (ppb) of mercury to in excess of 50,000 ppb of mercury, for instance 2 to 10,000 ppb of mercury; or 5 to 1000 ppb of mercury. The mercury content of naturally occurring hydrocarbon fluids may take a variety of forms, and the present invention can be applied to the removal of elemental mercury, particulate mercury, organic mercury or ionic mercury from hydrocarbon fluids. In one preferred embodiment, the mercury is in one or more of elemental, particulate or organic form. Still more preferably, the mercury is in elemental or organic form. Thus, in one embodiment, the mercury is in elemental form. In a further embodiment, the mercury is in organic form.

The process of the invention may be applied to substantially any hydrocarbon feed which comprises mercury, and which is liquid or gaseous under the operating conditions of the process. Thus, hydrocarbon fluids that may be processed according to the present invention include liquid hydrocarbons, such as liquefied natural gas; light distillates, e.g. comprising liquid petroleum gas, gasoline, and/or naphtha; natural gas condensates; middle distillates, e.g. comprising kerosene and/or diesel; heavy distillates, e.g. fuel oil; and crude oils. Hydrocarbon fluids that may be processed according to the present invention also include gaseous hydrocarbons, such as natural gas and refinery gas. Preferably the hydrocarbon fluid comprises a liquid hydrocarbon.

In accordance with the present invention, [Cat$^+$] may comprise a cationic species selected from: ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium, and uronium.

In one preferred embodiment of the invention, [Cat$^+$] comprises an aromatic heterocyclic cationic species selected from: benzimidazolium, benzofuranium, benzothiophenium, benzotriazolium, cinnolinium, diazabicyclodecenium, diazabicyclononenium, diazabicyclo-undecenium, dithiazolium, imidazolium, indazolium, indolinium, indolium, oxazinium, oxazolium, iso-oxazolium, oxathiazolium, phthalazinium, pyrazinium, pyrazolium, pyridazinium, pyridinium, pyrimidinium, quinazolinium, quinolinium, iso-quinolinium, quinoxalinium, tetrazolium, thiadiazolium, iso-thiadiazolium, thiazinium, thiazolium, iso-thiazolium, triazinium, triazolium, and iso-triazolium.

More preferably, [Cat$^+$] has the formula:

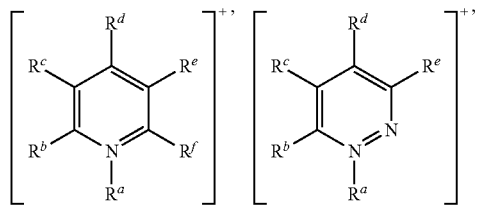

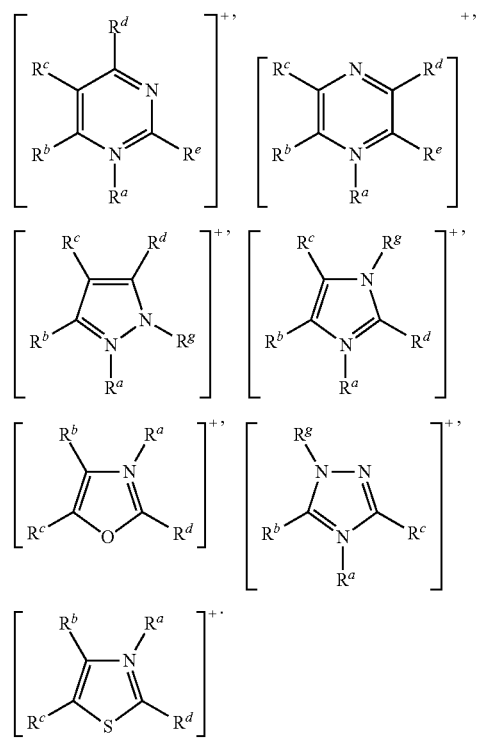

wherein: $R^a$, $R^b$, $R^c$, $R^d$, $R^e$, $R^f$ and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —(CH$_2$)$_q$— wherein q is from 3 to 6; and wherein said alkyl, cycloalkyl or aryl groups or said methylene chain are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO$_2$, —CO$_2$R$^x$, —OC(O)R$^x$, —C(O)R$^x$, —C(S)R$^x$, —CS$_2$R$^x$, —SC(S)R$^x$, —S(O) (C$_1$ to C$_6$)alkyl, —S(O)O(C$_1$ to C$_6$)alkyl, —OS(O)(C$_1$ to C$_6$)alkyl, —S(C$_1$ to C$_6$)alkyl, —S—S(C$_1$ to C$_6$ alkyl), —NR$^x$C(O)NR$^y$R$^z$, —NR$^x$C(O)OR$^y$, —OC(O) NR$^y$R$^z$, —NR$^x$C(S)OR$^y$, —OC(S)NR$^y$R$^z$, —NR$^x$C(S) SR$^y$, —SC(S)NR$^y$R$^z$, —NR$^x$C(S)NR$^y$R$^z$, —C(O) NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl.

$R^a$ is preferably selected from $C_1$ to $C_{30}$, linear or branched, alkyl, more preferably $C_2$ to $C_{20}$ linear or branched alkyl, still more preferably, $C_2$ to $C_{10}$ linear or branched alkyl, and most preferably $C_4$ to $C_8$ linear or branched alkyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_2$ to $C_{20}$ linear or branched alkyl, still more preferably, $C_2$ to $C_{10}$ linear or branched alkyl, and most preferably $C_4$ to $C_8$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_{15}$ alkoxyalkyl.

In further preferred embodiments, $R^b$, $R^c$, $R^d$, $R^e$, and $R^f$ are independently selected from hydrogen and $C_1$ to $C_5$ linear or branched alkyl, and more preferably $R^b$, $R^c$, $R^d$, $R^e$, and $R^f$ are hydrogen.

In this embodiment of the invention, [Cat$^+$] preferably comprises a cation selected from:

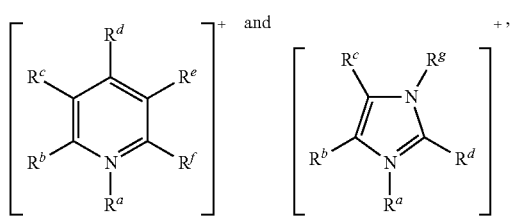

wherein: $R^a$, $R^b$, $R^c$, $R^d$, $R^e$, $R^f$, and $R^g$ are as defined above.

More preferably, [Cat$^+$] comprises a cation selected from:

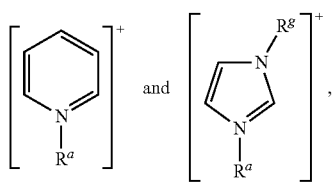

wherein: $R^a$ and $R^g$ are as defined above.

Also in accordance with this embodiment of the invention, [Cat$^+$] may preferably comprise a cation selected from:

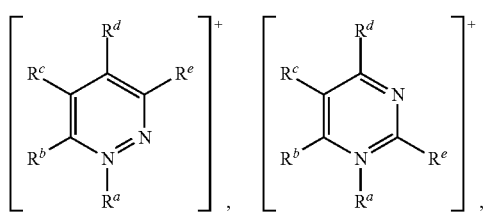

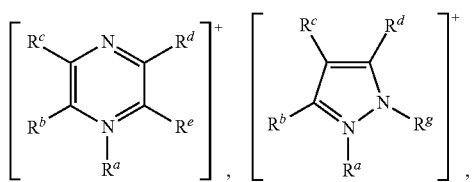

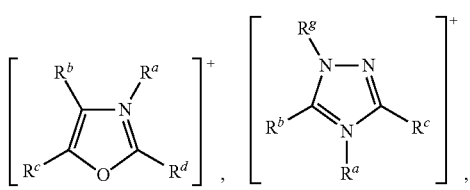

wherein: $R^a$, $R^b$, $R^c$, $R^d$, $R^e$, $R^f$ and $R^g$ are as defined above.

Specific examples of preferred nitrogen-containing aromatic heterocyclic cations that may be used according to the present invention include:

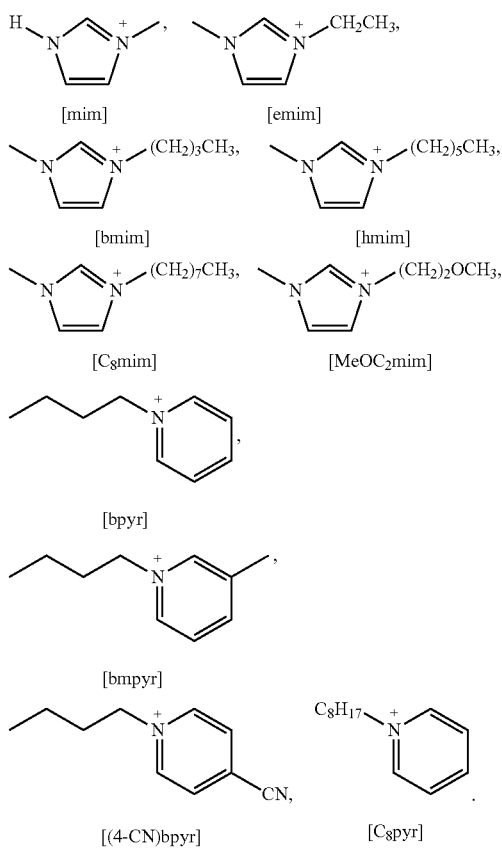

In another preferred embodiment of the invention, [Cat$^+$] comprises a saturated heterocyclic cation selected from cyclic ammonium, 1,4-diazabicyclo[2.2.2]octanium, morpholinium, cyclic phosphonium, piperazinium, piperidinium, quinuclidinium, and cyclic sulfonium.

More preferably, [Cat$^+$] comprises a saturated heterocyclic cation having the formula:

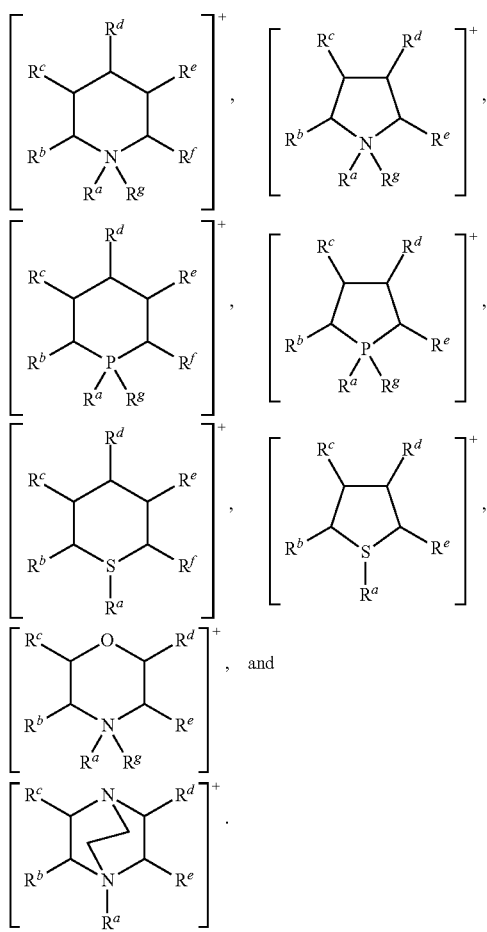

wherein: $R^a$, $R^b$, $R^c$, $R^d$, $R^e$, $R^f$, and $R^g$ are as defined above.

Still more preferably, [Cat$^+$] comprises a saturated heterocyclic cation having the formula:

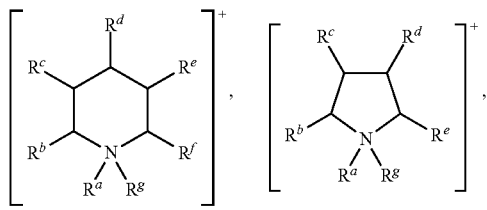

and is most preferably

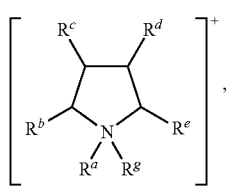

wherein: $R^a$, $R^b$, $R^c$, $R^d$, $R^e$, $R^f$, and $R^g$ are as defined above.

Also in accordance with this embodiment of the invention, [Cat$^+$] may preferably comprise a saturated heterocyclic cation selected from:

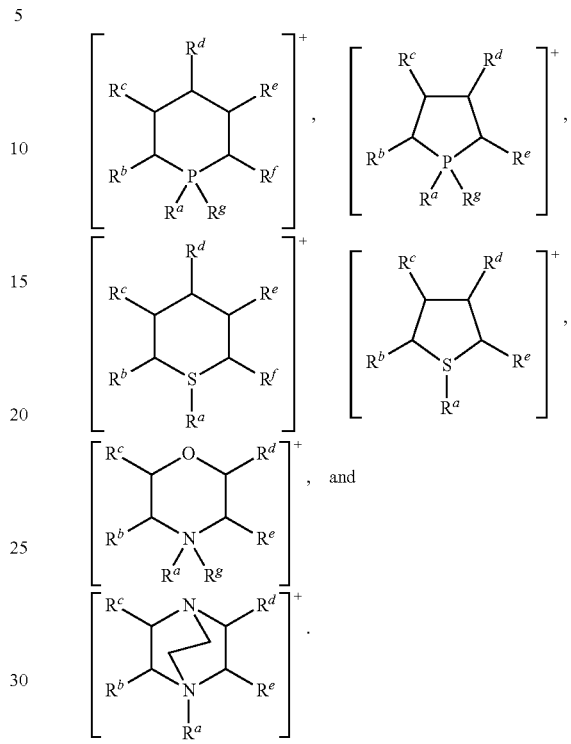

In the saturated heterocyclic cations above, $R^a$ is preferably selected from $C_1$ to $C_{30}$, linear or branched, alkyl, more preferably $C_2$ to $C_{20}$ linear or branched alkyl, still more preferably, $C_2$ to $C_{10}$ linear or branched alkyl, and most preferably $C_4$ to $C_8$ linear or branched alkyl. Further examples include wherein $R^a$ is selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl.

In the saturated heterocyclic cations comprising an $R^g$ group, $R^g$ is preferably selected from $C_1$ to $C_{10}$ linear or branched alkyl, more preferably, $C_1$ to $C_5$ linear or branched alkyl, and most preferably $R^g$ is a methyl group.

In the saturated heterocyclic cations comprising both an $R^a$ and an $R^g$ group, $R^a$ and $R^g$ are each preferably independently selected from $C_1$ to $C_{30}$, linear or branched, alkyl, and one of $R^a$ and $R^g$ may also be hydrogen. More preferably, one of $R^a$ and $R^g$ may be selected from $C_2$ to $C_{20}$ linear or branched alkyl, still more preferably, $C_2$ to $C_{10}$ linear or branched alkyl, and most preferably $C_4$ to $C_8$ linear or branched alkyl, and the other one of $R^a$ and $R^g$ may be selected from $C_1$ to $C_{10}$ linear or branched alkyl, more preferably, $C_1$ to $C_5$ linear or branched alkyl, and most preferably a methyl group. In a further preferred embodiment, $R^a$ and $R^g$ may each be independently selected, where present, from $C_1$ to $C_{30}$ linear or branched alkyl and $C_1$ to $C_{15}$ alkoxyalkyl.

In further preferred embodiments, $R^b$, $R^c$, $R^d$, $R^e$, and $R^f$ are independently selected from hydrogen and $C_1$ to $C_5$ linear or branched alkyl, and more preferably $R^b$, $R^c$, $R^d$, $R^e$, and $R^f$ are hydrogen.

In another preferred embodiment of the invention, [Cat⁺] comprises an acyclic cation selected from:

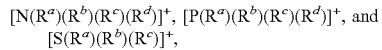

wherein: $R^a$, $R^b$, $R^c$, and $R^d$ are each independently selected from a $C_1$ to $C_{30}$, straight chain or branched alkyl group, a $C_3$ to $C_8$ cycloalkyl group, or a $C_6$ to $C_{10}$ aryl group; and wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO₂, —CO₂$R^x$, —OC(O)$R^x$, —C(O)$R^x$, —C(S)$R^x$, —CS₂$R^x$, —SC(S)$R^x$, —S(O)($C_1$ to $C_6$)alkyl, —S(O)P($C_1$ to $C_6$)alkyl, —OS(O)($C_1$ to $C_6$)alkyl, —S($C_1$ to $C_6$)alkyl, —S—S($C_1$ to $C_6$ alkyl), —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl.

More preferably, [Cat⁺] comprises a cation selected from:

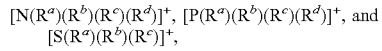

wherein: $R^a$, $R^b$, $R^c$, and $R^d$ are each independently selected from a $C_1$ to $C_{15}$ straight chain or branched alkyl group, a $C_3$ to $C_6$ cycloalkyl group, or a $C_6$ aryl group; and wherein said alkyl, cycloalkyl or aryl groups are unsubstituted or may be substituted by one to three groups selected from: $C_1$ to $C_6$ alkoxy, $C_2$ to $C_{12}$ alkoxyalkoxy, $C_3$ to $C_5$ cycloalkyl, $C_6$ to $C_{10}$ aryl, $C_7$ to $C_{10}$ alkaryl, $C_7$ to $C_{10}$ aralkyl, —CN, —OH, —SH, —NO₂, —CO₂$R^x$, —OC(O)$R^x$, —C(O)$R^x$, —C(S)$R^x$, —CS₂$R^x$, —SC(S)$R^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S($C_1$ to $C_6$ alkyl), —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl.

Further examples include wherein $R^a$, $R^b$, $R^c$ and $R^d$ are independently selected from methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl. More preferably two or more, and most preferably three or more, of $R^a$, $R^b$, $R^c$ and $R^d$ are selected from methyl, ethyl, propyl and butyl.

Still more preferably, [Cat⁺] comprises a cation selected from:

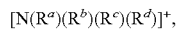

wherein: $R^a$, $R^b$, $R^c$, and $R^d$ are as defined above.

In a preferred further embodiment, [Cat⁺] preferably comprises a cation selected from:

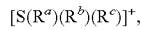

wherein: $R^a$, $R^b$, $R^c$, and $R^d$ are as defined above.

Specific examples of preferred ammonium and phosphonium cations suitable for use according to the present invention include:

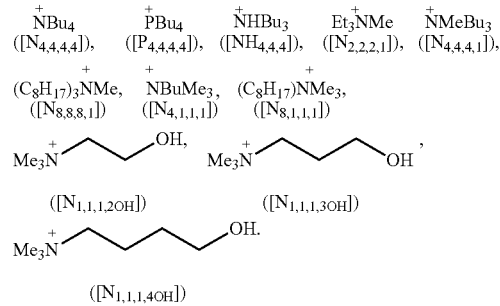

In a further embodiment of the invention, [Cat⁺] comprises a cation selected from guanidinium, cyclic guanidinium, uronium, cyclic uronium, thiuronium and cyclic thiuronium. More preferably, [Cat⁺] comprises a cation having the formula:

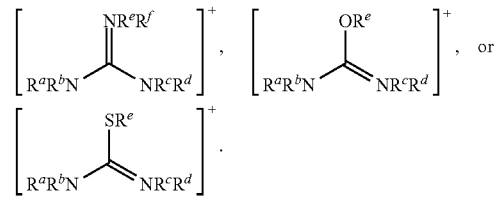

wherein: $R^a$, $R^b$, $R^c$, $R^d$, $R^e$, and $R^f$ are each independently selected from a $C_1$ to $C_{30}$, straight chain or branched alkyl group, a $C_3$ to $C_8$ cycloalkyl group, or a $C_6$ to $C_{10}$ aryl group, or any two of $R^a$, $R^b$, $R^c$, and $R^d$, attached to different nitrogen atoms form a methylene chain —(CH₂)$_q$— wherein q is from 2 to 5; wherein said alkyl, cycloalkyl or aryl groups or said methylene chain are unsubstituted or may be substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO₂, —CO₂$R^x$, —OC(O)$R^x$, —C(O)$R^x$, —C(S)$R^x$, —CS₂$R^x$, —SC(S)$R^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S($C_1$ to $C_6$ alkyl), —NR$^x$C(O)NR$^y$R$^z$, —NR$^x$C(O)OR$^y$, —C(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl.

Specific examples of guanidinium, uronium, and thiuronium cations suitable for use according to the present invention include:

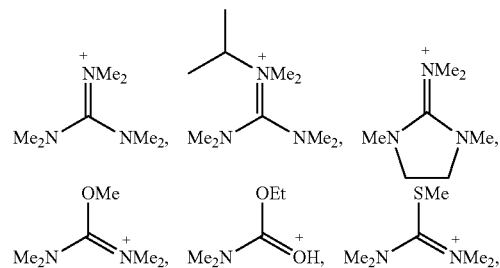

-continued

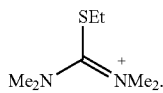

In a further preferred embodiment, [Cat⁺] comprises a cation comprising an electron-rich sulfur or selenium moiety. Examples include cations as defined above comprising pendant thiol, thioether, or disulfide substituents.

In accordance with the present invention, [X⁻] may comprise one or more anions selected from halides, perhalides, pseudohalides, sulphates, sulphites, sulfonates, sulfonimides, phosphates, phosphites, phosphonates, methides, borates, carboxylates, azolates, carbonates, carbamates, thiophosphates, thiocarboxylates, thiocarbamates, thiocarbonates, xanthates, thiosulfonates, thiosulfates, nitrate, nitrite, perchlorate, halometallates, amino acids and borates.

Thus, [X⁻] may represent one or more anions selected from:
a) a halide anion selected from: F⁻, Cl⁻, Br⁻, I⁻;
b) a perhalide anion selected from: [I₃]⁻, [I₂Br]⁻, [IBr₂]⁻, [Br₃]⁻, [Br₂C]⁻, [BrCl₂]⁻, [I—Cl₂]⁻, [I₂Cl]⁻, [Cl₃]⁻;
c) a pseudohalide anion selected from: [N₃]⁻, [NCS]⁻, [NCSe]⁻, [NCO]⁻, [CN]⁻;
d) a sulphate anion selected from: [HSO₄]⁻, [SO₄]²⁻, [R²OSO₂O]⁻;
e) a sulphite anion selected from: [HSO₃]⁻, [SO₃]²⁻, [R²OSO₂]⁻;
f) a sulfonate anion selected from: [R¹SO₂O]⁻;
g) a sulfonimide anion selected from: [(R¹SO₂)₂N]⁻;
h) a phosphate anion selected from: [H₂PO₄]⁻, [HPO₄]²⁻, [PO₄]³⁻, [R²OPO₃]²⁻, [(R²O)₂PO₂],
i) a phosphite anion selected from: [H₂PO₃]⁻, [HPO₃]²⁻, [R²OPO₂]²⁻, [(R²O)₂PO]⁻;
j) a phosphonate anion selected from: [R¹PO₃]²⁻, [R¹P(O)(OR²)O]⁻;
k) a methide anion selected from: [(R¹SO₂)₃]⁻;
l) a borate anion selected from: [bisoxalatoborate], [bismalonatoborate];
m) a carboxylate anion selected from: [R²CO₂]⁻;
n) an azolate anion selected from: [3,5-dinitro-1,2,4-triazolate], [4-nitro-1,2,3-triazolate], [2,4-dinitroimidazolate], [4,5-dinitroimidazolate], [4,5-dicyano-imidazolate], [4-nitroimidazolate], [tetrazolate];
o) a sulfur-containing anion selected from: thiocarbonates (e.g. [R²OCS₂]); thiocarbamates and (e.g. [R²₂NCS₂]⁻); thiocarboxylates (e.g. [R¹CS₂]⁻); thiophosphates (e.g. [(R²O)₂PS₂]⁻); thiosulfonates (e.g. [RS(O)₂S]⁻); and thiosulfates (e.g. [ROS(O)₂S]⁻; and
p) a nitrate ([NO₃]⁻) or nitrite ([NO₂]⁻) anion;
wherein: R¹ and R² are independently selected from the group consisting of $C_1$-$C_{10}$ alkyl, $C_6$ aryl, $C_1$-$C_{10}$ alkyl($C_6$)aryl, and $C_6$ aryl($C_1$-$C_{10}$)alkyl each of which may be substituted by one or more groups selected from: fluoro, chloro, bromo, iodo, $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO₂, —CO₂Rˣ, —OC(O)Rˣ, —C(O)Rˣ, —C(S)Rˣ, —CS₂Rˣ, —SC(S)Rˣ, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S($C_1$ to $C_6$ alkyl), —NRˣC(O)NRʸRᶻ, —NRˣC(O)ORʸ, —OC(O)NRʸRᶻ, —NRˣC(S)ORʸ, —OC(S)NRʸRᶻ, —NRˣC(S)SRʸ, —SC(S)NRʸRᶻ, —NRˣC(S)NRʸRᶻ, —C(O)NRʸRᶻ, —C(S)NRʸRᶻ, —NRʸRᶻ, or a heterocyclic group, wherein Rˣ, Rʸ and Rᶻ are independently selected from hydrogen or $C_1$ to $C_6$ alkyl, and wherein R¹ may also be fluorine, chlorine, bromine or iodine.

In one preferred embodiment, [X⁻] comprises a halide or perhalide anion selected from: [F]⁻, [Cl]⁻, [Br]⁻, [I]⁻, [I₃]⁻, [I₂Br]⁻, [IBr₂]⁻, [Br₃]⁻, [Br₂Cl]⁻, [BrCl₂]⁻, [ICl₂]⁻, [I₂Cl]⁻, [Cl₃]⁻. More preferably [X–] comprises a halide or perhalide anion selected from: [F]⁻, [Cl]⁻, [Br]⁻, [I]⁻, [I₂Br]⁻, [IBr₂]⁻, [Br₂Cl]⁻, [BrCl₂]⁻, [ICl₂]⁻, [I₂Cl]⁻.

In a further preferred embodiment, [X⁻] comprises an oxygen-containing anion selected from: [NO₃]⁻, [NO₂]⁻, [H₂PO₄]⁻, [HPO₄]²⁻, [PO₄]³⁻, [R²OPO₃]²⁻, [(R²O)₂PO₂]⁻, [H₂PO₃]⁻, [HPO₃]²⁻, [R²OPO₂]²⁻, [(R²O)₂PO]⁻, [R¹PO₃]²⁻, [R¹P(O)(OR²)O]⁻, wherein R¹ and R² are as defined above. Further examples of anions in this category include: [MeOPO₃]²⁻, [EtOPO₃]²⁻, [(MeO)₂PO₂]⁻, [(EtO)₂PO₂]⁻, [MePO₃]²⁻, [EtPO₃]²⁻, [MeP(O)(OMe)O]⁻, [EtP(O)(OEt)O]⁻.

In a further preferred embodiment, [X⁻] comprises a carboxylate anion selected from [R²CO₂]⁻, wherein R² is as defined above. Further examples of anions in this category include: [HCO₂]⁻, [MeCO₂]⁻, [EtCO₂]⁻, [CH₂(OH)CO₂]⁻, [CH₃CH(OH)CH₂CO₂]⁻, [PhCO₂]⁻, salicylate, alaninate, argininate, asparaginate, aspartate, cysteinate, glutamate, glutaminate, glycinate, histidinate, isoleucinate, leucinate, lysinate, methioninate, phenylalaninate, prolinate, serinate, threoninate, tryptophanate, tyrosinate, valinate, N-methyl-glycinate, 2-aminobutyrate, 2-aminoisobutyrate, 2-amino-4-aminooxy-butyrate, 2-(methylguanidino)-ethanoate, 2-pyrrolidone-5-carboxylate, piperidine-2-carboxylate, and 1-piperidinepropionate, In a further preferred embodiment, [X⁻] comprises an anion comprising an electron-rich sulfur or selenium moiety. Examples include: anions as defined above comprising pendant thiol, thioether, or disulfide substituents, [NCS]⁻, [NCSe]⁻, [R²OCS₂]⁻, [R²₂NCS₂]⁻, [R¹CS₂]⁻, [(R²O)₂PS₂]⁻, [R¹S(O)₂S]⁻ and [R²OS(O)₂S]⁻, wherein R¹ and R² are as defined above. Further examples of anions in this category include: [CH₂(SH)CO₂]⁻, [CH₃CH₂(SH)CO₂]⁻, [CH₃CS₂]⁻, [CH₃CH₂CS₂]⁻, [PhCS₂]⁻, [(MeO)₂PS₂]⁻, [(EtO)₂PS₂]⁻, [(PhO)₂PS₂]⁻, [(CH₃)₂NCS₂]⁻, [(CH₃CH₂)₂NCS₂]⁻, [Ph₂NCS₂]⁻, [CH₃OCS₂]⁻, [CH₃CH₂OCS₂]⁻, [PhOCS₂]⁻,

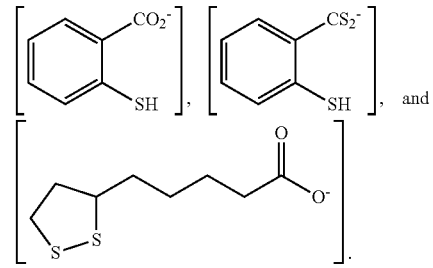

In a further preferred embodiment, [X⁻] comprises a sulfur-containing anion selected from sulphate anions ([HSO₄]⁻, [SO₄]²⁻, [R²OSO₂O]⁻), sulphite anions ([HSO₃]⁻, [SO₃]²⁻, [R²OSO₂]⁻) and sulfonate anions ([R¹SO₂O]⁻). Further examples of anions in this category include: [FSO₂O]⁻, [CF₃SO₂O]⁻, [MeSO₂O]⁻, [PhSO₂O]⁻, [4-MeC₆H₄SO₂O]⁻, [dioctylsulfosuccinate]⁻, [MeOSO₂O]⁻, [EtOSO₂O]⁻, [C₈H₁₇OSO₂O]⁻, and [MeOSO₂]⁻, [PhOSO₂]⁻.

In a further embodiment of the invention, [X⁻] may comprise a fluorinated anion selected from: [BF$_4$], [CF$_3$BF$_3$]⁻, [CF$_3$CF$_2$BF$_3$]⁻, [PF$_6$]⁻, [CF$_3$PF$_5$]⁻, [CF$_3$CF$_2$PF$_5$]⁻, [(CF$_3$CF$_2$)$_2$PF$_4$]⁻; and [(CF$_3$CF$_2$)$_3$PF$_3$]⁻. However, fluorinated anions of this type are generally less preferred in comparison with the anion types disclosed above.

The present invention is not limited to ionic liquids comprising anions and cations having only a single charge. Thus, the formula [Cat⁺][X⁻] is intended to encompass ionic liquids comprising, for example, doubly, triply and quadruply charged anions and/or cations. The relative stoichiometric amounts of [Cat⁺] and [X⁻] in the ionic liquid are therefore not fixed, but can be varied to take account of cations and anions with multiple charges. For example, the formula [Cat⁺][X⁻] should be understood to include ionic liquids having the formulae [Cat⁺]$_2$[X²⁻]; [Cat²⁺][X⁻]$_2$; [Cat²⁺][X²⁻]; [Cat⁺]$_3$[X³⁻]; [Cat³⁺][X⁻]$_3$ and so on.

It will also be appreciated that the present invention is not limited to ionic liquids comprising a single cation and a single anion. Thus, [Cat⁺] may, in certain embodiments, represent two or more cations, such as a statistical mixture of 1,3-dimethylimidazolium, 1-ethyl-3-methylimidazolium and 1-3-diethylimidazolium. Similarly, [X⁻] may, in certain embodiments, represent two or more anions, such as a mixture of tribromide ([Br$_3$]⁻) and bistriflimide ([N(SO$_2$CF$_3$)$_2$]⁻).

Ionic liquids for use according to the present invention preferably have a melting point of 250° C. or less, more preferably 150° C. or less, still more preferably 100° C. or less, still more preferably 80° C. or less, and most preferably, the ionic liquid has a melting point below 30° C. However, any compound that meets the criteria of being a salt (consisting of a cation and an anion) and which is liquid at the operating temperature and pressure of the process, or exists in a fluid state during any stage of the reaction, may be defined as an ionic liquid for the purposes of the present invention. Most preferably, the ionic liquid is chosen so as to be substantially immiscible with the hydrocarbon fluid, particularly where the hydrocarbon fluid comprises a liquid hydrocarbon.

The ionic liquid is preferably contacted with the mercury-containing hydrocarbon fluid feed at a temperature of from −80° C. to 200° C., more preferably from −20° C. to 150° C., still more preferably from 15° C. to 100° C., and most preferably from 15° C. to 40° C. The ionic liquid and mercury-containing hydrocarbon fluid feed may be contacted at atmospheric pressure (approximately 100 kPa), although pressures above or below atmospheric pressure may be used if desired. For instance, the process may be conducted at a pressure of from 10 kPa to 10000 kPa, more preferably from 20 kPa to 1000 kPa, still more preferably 50 to 200 kPa, and most preferably 80 to 120 kPa.

As noted above, however, the ionic liquid must be liquid at the operating temperature and pressure of the process of the invention. Thus, the above operating temperature and pressure ranges may, in some cases, be further limited by the temperature and pressure ranges in which a selected ionic liquid is in liquid form.

Generally, it is most economical to contact the ionic liquid and the mercury-containing hydrocarbon fluid feed without the application of heat, and refinery product streams may be conveniently treated at the temperature at which they emerge from the refinery, which is typically up to 100° C.

The ionic liquid and the mercury-containing hydrocarbon fluid feed are preferably contacted in a hydrocarbon:ionic liquid volume ratio of from 1:1 to 10,000:1, more preferably from 20:1 to 10,000:1, more preferably from 100:1 to 10,000:1 and most preferably 1000:1 to 10,000:1. In general, a smaller volume of ionic liquid relative to the amount of hydrocarbon is preferred as this prevents the formation of emulsions.

In a further preferred embodiment, the ionic liquid:hydrocarbon volume ratio is selected such that 1 to 10,000 moles, more preferably 1 to 1000 moles, still more preferably 1 to 100 moles, still more preferably 1 to 10 moles, and most preferably 1 to 5 moles of the ionic liquid are contacted with the mercury-containing hydrocarbon fluid feed per mole of mercury in the mercury-containing hydrocarbon fluid feed.

In accordance with the process of the present invention, the ionic liquid extracts at least 60 wt % of the mercury content of the mercury-containing hydrocarbon fluid feed. More preferably, the ionic liquid extracts at least 70 wt %, still more preferably at least 80 wt %, still more preferably at least 90 wt %, still more preferably at least 95 wt %, and most preferably greater than 99 wt % of the mercury content of the mercury-containing hydrocarbon fluid feed.

Thus, in accordance with the process of the present invention, a hydrocarbon fluid product may be obtained which comprises 10% or less of the mercury content of the mercury-containing hydrocarbon fluid feed. More preferably the hydrocarbon fluid product comprises 5% or less of the mercury content of the mercury-containing hydrocarbon fluid feed, and most preferably the hydrocarbon fluid product comprises 1% or less of the mercury content of the mercury-containing hydrocarbon fluid feed. Preferably the mercury concentration of the hydrocarbon fluid product of the process of the invention is less than 50 ppb, more preferably less than 10 ppb, and most preferably less than 5 ppb.

The ionic liquid and the mercury-containing hydrocarbon fluid feed may be contacted by either continuous processes or batch processes. Any conventional liquid-liquid or gas-liquid contactor apparatus may be used in accordance with the present invention. For instance, the ionic liquid and the mercury-containing hydrocarbon fluid feed may be contacted using a counter-current liquid-liquid contactor, a co-current liquid-liquid contactor, a counter-current gas-liquid contactor, a co-current gas-liquid contactor, a liquid-liquid batch contactor, or a gas-liquid batch contactor.

In a further embodiment, the ionic liquid may be supported on a solid, preferably porous, carrier material prior to being contacted with the mercury-containing hydrocarbon fluid feed. Suitable solid carriers for use in this embodiment of the invention include silica alumina, silica-alumina, and activated carbon. In general, supported ionic liquids for use according to this embodiment of the invention comprise from 50% by weight to 1% by weight of ionic liquid, and more preferably 20% by weight to 1% by weight of ionic liquid.

In addition, the process may be repeated on the same mercury-containing hydrocarbon fluid feed in a series of contacting steps, e.g. two to ten, to obtain a successive reduction in the mercury content of the hydrocarbon fluid product at each step.

The ionic liquid is allowed to contact the mercury-containing hydrocarbon fluid feed for sufficient time to enable at least a portion of the mercury in the mercury-containing hydrocarbon fluid feed to transfer into the ionic liquid phase. Suitable timescales include from 1 minute to 60 minutes and more preferably from 2 minutes to 30 minutes.

The process of the present invention may used in combination with other known methods for the removal of mercury from hydrocarbon fluids. However, one advantage of the present invention is that it avoids the need for pre-treatment of the hydrocarbon fluid to remove solidified species prior to the mercury removal step.

In a further embodiment, the present invention provides a process for the preparation of a mercury-containing solution, comprising contacting a mercury-containing hydrocarbon fluid with an ionic liquid having the formula:

$$[Cat^+][X^-]$$

wherein [Cat$^+$] represents an cationic species, and
[X$^-$] represents an anionic species.

In this embodiment of the invention, [Cat$^+$] may be any of the ionic liquid cations described above, and those cations described as preferred above are also preferred in this embodiment of the invention. Similarly, [X$^-$] in this embodiment of the invention may be any of the ionic liquid anions described above, and those anions described as preferred above are also preferred in this embodiment of the invention.

In a further embodiment, the present invention provides a process for the removal of cadmium and/or lead from a cadmium- and/or lead-containing hydrocarbon fluid feed comprising the steps of:
(i) contacting the cadmium- and/or lead-containing hydrocarbon fluid feed with an ionic liquid having the formula:

$$[Cat^+][X^-]$$

wherein [Cat$^+$] represents one or more cationic species; and
[X$^-$] represents one or more anionic species; and
(ii) separating from the ionic liquid a hydrocarbon fluid product having a reduced cadmium and/or lead content compared to the cadmium- and/or lead-containing hydrocarbon feed In this embodiment of the invention, [Cat$^+$] may be any of the ionic liquid cations described above, and those cations described as preferred above are also preferred in this embodiment of the invention. Similarly, [X$^-$] in this embodiment of the invention may be any of the ionic liquid anions described above, and those anions described as preferred above are also preferred in this embodiment of the invention.

The present invention will now be described by way of example.

EXAMPLES

Removal of Mercury from a Natural Gas Condensate

In a test process, equal masses of a natural gas condensate (NGC) and ionic liquid were stirred for 4 hours at 25° C. The stirring was then stopped and the ionic liquid separated as a lower dense phase and the mixtures were left to stand for 15 hours to ensure equilibration. Multiple samples from the condensate phases (30 mg each) were taken without disturbing the liquid-liquid interface and the total mercury content determined using a Milestone DMA-80 pyrolysis/AA analyser. Mercury contents determined are shown in micrograms per kilogram with standard deviations from duplicate runs in parentheses.

After contacting natural gas condensate with all the ionic liquids described, the mercury content of the natural gas condensate was reduced to below 14 µg kg$^{-1}$ except in the case of contacting with 1-ethyl-3-methylimidazolium ethylsulfate.

Example 1: 1-butyl-3-methylimidazolium bis(trifluoromethane)sulfonimide

NGC (4.1 g) was mixed with 1-butyl-3-methylimidazolium bis(trifluoromethane)sulfonimide (4.1 g). The mercury content of the condensate phase after contacting was 7 (3) µg kg$^{-1}$ compared to the NGC control sample that contained 99 (10) µg kg$^{-1}$ of mercury.

Example 2: 1-butyl-3-methylimidazolium chlorodibromide

NGC (4.2 g) was mixed with 1-butyl-3-methylimidazolium chlorodibromide (4.2 g). The mercury content of the condensate phase after contacting was 11 (9) µg kg$^{-1}$ compared to the NGC control sample that contained 99 (10) µg kg$^{-1}$ of mercury.

Example 3: 1-ethyl-3-methylimidazolium ethylsulfate

NGC (4.1 g) was mixed with 1-ethyl-3-methylimidazolium ethylsulfate (4.0 g). The mercury content of the condensate phase after contacting was 73 (13) µg kg$^{-1}$ compared to the NGC control sample that contained 99 (10) µg kg$^{-1}$ of mercury.

Example 4: 1-hexyl-3-methylimidazolium bis(trifluoromethane)sulfonimide

NGC (2.0 g) was mixed with 1-hexyl-3-methylimidazolium bis(trifluoromethane)sulfonimide (2.0 g). The mercury content of the condensate phase after contacting was 4 (1) µg kg$^{-1}$ compared to the NGC control sample that contained 99 (10) µg kg$^{-1}$ of mercury.

Example 5: 1-butyl-4-cyanopyridinium bis(trifluoromethane)sulfonimide

NGC (2.0 g) was mixed with 1-butyl-4-cyanopyridinium bis(trifluoromethane)sulfonimide (2.0 g). The mercury content of the condensate phase after contacting was 7 (5) µg kg$^{-1}$ compared to the NGC control sample that contained 99 (10) µg kg$^{-1}$ of mercury.

Example 6: 1-butyl-3-methylimidazolium diethyldithiophosphate

NGC (4.0 g) was mixed with 1-butyl-3-methylimidazolium diethyldithiophosphate (4.0 g). The mercury content of the condensate phase after contacting was 5 (5) µg kg$^{-1}$ compared to the initial NGC sample that contained 532 (23) µg kg$^{-1}$ of mercury.

Example 7: 1-butyl-3-methylimidazolium thiocyanate

NGC (4.0 g) was mixed with 1-butyl-3-methylimidazolium thiocyanate (4.0 g). The mercury content of the condensate phase after contacting was 5 (1) µg kg$^{-1}$ compared to the initial NGC sample that contained 532 (23) µg kg$^{-1}$ of mercury.

Example 8: 1-butyl-3-methylimidazolium methoxytri(propylene glycol)sulfate

NGC (4.0 g) was mixed with 1-butyl-3-methylimidazolium methoxytri(propylene glycol)sulfate (4.0 g). The mercury content of the condensate phase after contacting was 9 (4) µg kg$^{-1}$ compared to the initial NGC sample that contained 532 (23) µg kg$^{-1}$ of mercury.

Example 9: 1-butyl-3-methylimidazolium acetate

NGC (4.0 g) was mixed with 1-butyl-3-methylimidazolium acetate (4.0 g). The mercury content of the condensate phase after contacting was 14 µg kg$^{-1}$ compared to the initial NGC sample that contained 532 (23) µg kg$^{-1}$ of mercury.

Example 10: 1-ethyl-3-methylimidazolium hydrogensulfate

NGC (4.0 g) was mixed with 1-ethyl-3-methylimidazolium hydrogensulfate (4.0 g). The mercury content of the condensate phase after contacting was 8 (5) µg kg$^{-1}$ compared to the initial NGC sample that contained 532 (23) µg kg$^{-1}$ of mercury.

Removal of Mercury from Dodecane Spiked with Elemental Mercury

In test processes, known masses of dodecane that had been previously saturated with mercury with an ionic liquid were stirred with ionic liquids at a fixed temperature for a measured period of time. The stirring was then stopped and the ionic liquid separated as a lower dense phase and the mixtures were left to stand for 15 min. to ensure separation of the phases. Multiple samples from the condensate phases (30 mg each) were taken without disturbing the liquid-liquid interface and the total mercury content determined using a Milestone DMA-80 pyrolysis/AA analyser. Mercury contents determined are shown in micrograms per kilogram with standard deviations from duplicate runs in parentheses.

Example 11: Removal of Mercury from Dodecane with 1-butyl-3-methylimidazolium thiocyanate Dodecane (20 g) containing 3978 µg kg$^{-1}$ of mercury was stirred with 1-butyl-3-methylimidazolium thiocyanate (2.0 g) at 60° C. for 15 h. The mercury content of the dodecane phase decreased to 20 (5) µg kg$^{-1}$ and the mercury content of the ionic liquid extractant increased to 53143 (2830) µg kg$^{-1}$.

Example 12: Removal of Mercury from Dodecane with 1-butyl-3-methylimidazolium thiocyanate Dodecane (20 g) containing 3978 µg kg$^{-1}$ of mercury was stirred with 1-butyl-3-methylimidazolium thiocyanate (0.2 g) at 60° C. for 15 h. The mercury content of the dodecane phase decreased to 35 (2) µg kg$^{-1}$, the dodecane was decanted off and a further batch of dodecane containing 4551 µg kg$^{-1}$ of mercury was added and stirred for 18 h. The mercury content of the dodecane decreased to 43 (4) µg kg$^{-1}$.

Example 13: Removal of Mercury from Dodecane with 1-methylimidazolium camphor sulfonate Dodecane (2.4 g) containing 3500 µg kg$^{-1}$ of mercury was stirred with 1-5 methylimidazolium camphor sulfonate (1.2 g) at 21° C. for 6 h. The mercury content of the dodecane phase decreased to 60 µg kg$^{-1}$. The concentration of mercury in the dodecane phase remained constant after stirring was continued for 24 hours.

Example 14: Removal of Mercury from Dodecane with Tributylammonium Lipoate

Dodecane (3.1 g) containing 3500 µg kg$^{-1}$ of mercury was stirred with tributylammonium lipoate (2.2 g) at 21° C. for 6 h. The mercury content of the dodecane phase decreased to 95 µg kg$^{-1}$. After stirring for 24 hours, the concentration of mercury in the dodecane phase was reduced to 30 µg kg$^{-1}$. The concentration of mercury in the dodecane phase remained constant after stirring was continued for a further 24 hours.

Example 15: Removal of Mercury from Dodecane with Tricaprylmethylammonium Dithiobenzoate Dodecane (4.5 g) containing 3500 µg kg$^{-1}$ of mercury was stirred with tricaprylmethylammonium dithiobenzoate (1.2 g) at 50° C. for 24 h. The mercury content of the dodecane phase decreased to 40 µg kg$^{-1}$.

Example 16: Removal of Mercury from Dodecane with Tetrabutylphosphonium Dithiobutyrate Dodecane (1.4 g) containing 3500 µg kg$^{-1}$ of mercury was stirred with tetrabutylphosphonium dithiobutyrate (1.1 g) at 50° C. for 24 h. The mercury content of the dodecane phase decreased to 190 µg kg$^{-1}$. After stirring for a further 24 hours, the concentration of mercury in the dodecane phase was reduced to 80 µg kg$^{-1}$.

Example 17: Removal of Mercury from Dodecane with Choline Lipoate

Dodecane (3.0 g) containing 3500 µg kg$^{-1}$ of mercury was stirred with choline lipoate (0.9 g) at 50° C. for 24 h. The mercury content of the dodecane phase decreased to 290 µg kg$^{-1}$.

Example 18: Removal of Mercury from Dodecane with 1-butyl-3-methylimidazolium salicylate Dodecane (4.0 g) containing 3500 µg kg$^{-1}$ of mercury was stirred with 1-butyl-3-methylimidazolium salicylate (2.9 g) at 50° C. for 48 h. The mercury content of the dodecane phase decreased to 220 µg kg$^{-1}$.

Example 19: Removal of Mercury from Dodecane with Choline Decanoate

Dodecane (3.0 g) containing 3500 µg kg$^{-1}$ of mercury was stirred with choline decanoate (1.5 g) at 50° C. for 48 h. The mercury content of the dodecane phase decreased to 270 µg kg$^{-1}$.

Example 20: Removal of Mercury from Dodecane with 1-butyl-1-methylpyrrolidinium tris(pentafluoroethyptrifluorophosphate Dodecane (1.57 g) containing 2200 ppb of elemental mercury was stirred with 1-butyl-1-methylpyrrolidinium tris(pentafluoroethyl)trifluorophosphate (0.53 g) at 60° C. for 24 h. The mercury content of the dodecane phase decreased to 1587 ppb and the mercury content of the ionic liquid extractant increased to 963 ppm (28% of the available mercury was extracted into the ionic liquid).

The invention claimed is:

1. A process for the removal of mercury from a mercury-containing hydrocarbon fluid feed comprising the steps of:
   (i) contacting the mercury-containing hydrocarbon fluid feed with an ionic liquid in a hydrocarbon:ionic liquid volume ratio of from 100:1 to 10,000:1, the ionic liquid having the formula [Cat⁺][X⁻]; and
   (ii) separating from the ionic liquid a hydrocarbon fluid product having a reduced mercury content compared to the mercury-containing hydrocarbon feed;
   wherein [Cat⁺] comprises a cationic species selected from the group consisting of:

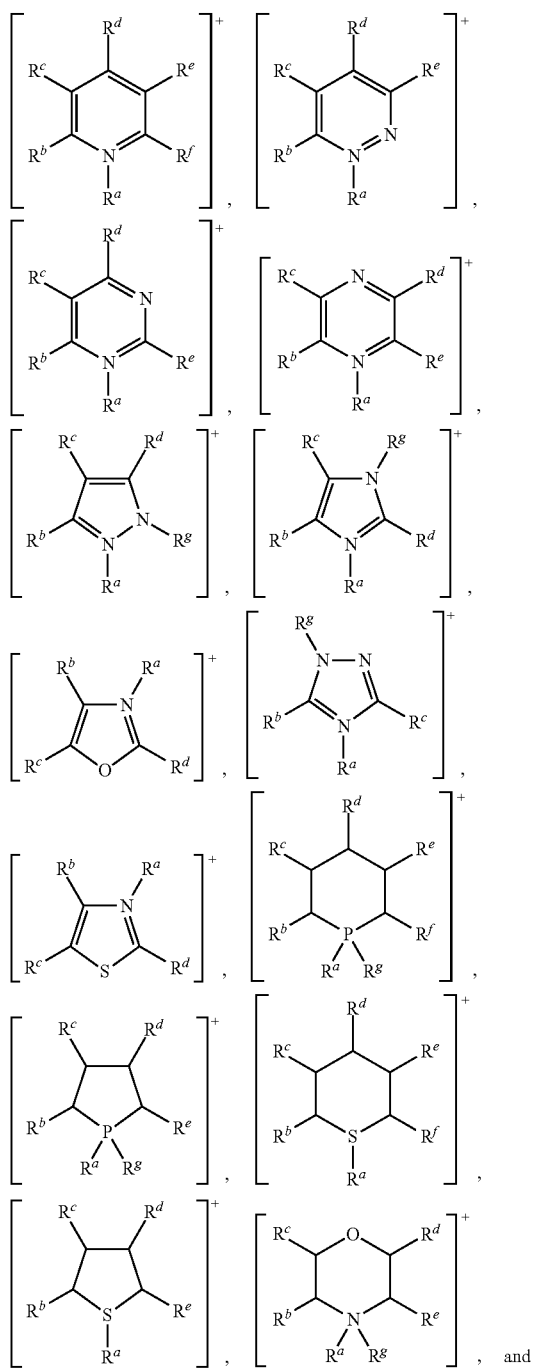

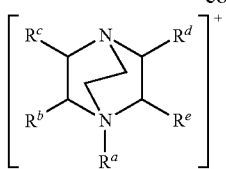

wherein $R^a$, $R^b$, $R^c$, $R^d$, $R^e$, $R^f$, and $R^g$ are each independently selected from hydrogen, a $C_1$ to $C_{30}$, straight chain or branched alkyl group, a $C_3$ to $C_8$ cycloalkyl group, or a $C_6$ to $C_{10}$ aryl group, or any two of $R^b$, $R^c$, $R^d$, $R^e$ and $R^f$ attached to adjacent carbon atoms form a methylene chain —$(CH_2)_q$— wherein q is from 3 to 6; and wherein said alkyl, cycloalkyl or aryl groups, or said methylene chain are unsubstituted or substituted by one to three groups selected from: $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO₂, —CO₂$R^x$, —OC(O)$R^x$, —C(O)$R^x$, —C(S)$R^x$, —CS₂$R^x$, —SC(S)$R^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S($C_1$ to $C_6$ alkyl), —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl; and wherein [X⁻] comprises an anion selected from [I₃]⁻, [I₂Br]⁻, [IBr₂]⁻, [Br₃]⁻, [Br₂Cl]⁻, [BrCl₂]⁻, [ICl₂]⁻, [I₂Cl]⁻, [Cl₃]⁻, [N₃]⁻, [NCS]⁻, [NCSe]⁻, [NCO]⁻, [CN]⁻, [HSO₄]⁻, [SO₄]²⁻, [R²OSO₂O]⁻, [HSO₃]⁻, [SO₃]²⁻, [R²OSO₂]⁻, [R¹SO₂O]⁻, [(R¹SO₂)₂N]⁻, [H₂PO₄]⁻, [HPO₄]²⁻, [PO₄]³⁻, [R²OPO₃]²⁻, [(R²O)₂PO₂]⁻, [H₂PO₃]⁻, [HPO₃]²⁻, [R²OPO₂]²⁻, [(R²O)₂PO]⁻, [R¹PO₃]²⁻, [R¹P(O)(OR²)O]⁻, [(R¹SO₂)₃C]⁻, [bisoxalatoborate], [bismalonatoborate], [R²CO₂]⁻, [3,5-dinitro-1,2,4-triazolate], [4-nitro-1,2,3-triazolate], [2,4-dinitroimidazolate], [4,5-dinitroimidazolate], [4,5-dicyano-imidazolate], [4-nitroimidazolate], [tetrazolate], [R²OCS₂]⁻, [R²₂NCS₂]⁻, [R¹CS₂]⁻, [(R²O)₂PS₂]⁻, [RS(O)₂S]⁻, [ROS(O)₂S]⁻, [NO₃], and [NO₂]⁻; wherein R¹ and R² are independently selected from the group consisting of $C_1$-$C_{10}$ alkyl, $C_6$ aryl, $C_1$-$C_{10}$ alkyl($C_6$) aryl, and $C_6$ aryl($C_1$-$C_{10}$)alkyl each of which is unsubstituted or substituted by one or more groups selected from: fluoro, chloro, bromo, iodo, $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO₂, —CO₂$R^x$, —OC(O)$R^x$, —C(O)$R^x$, —C(S)$R^x$, —CS₂$R^x$, —SC(S)$R^x$, —S(O)($C_1$ to $C_6$)alkyl, —S(O)O($C_1$ to $C_6$)alkyl, —OS(O)($C_1$ to $C_6$)alkyl, —S($C_1$ to $C_6$)alkyl, —S—S($C_1$ to $C_6$ alkyl), —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$ to $C_6$ alkyl, and wherein R¹ may also be fluorine, chlorine, bromine or iodine.

2. A process according to claim 1, wherein the mercury is in elemental, particulate, or organic form.

3. A process according to claim 1, wherein the mercury concentration in the mercury-containing hydrocarbon fluid feed is from about 1 to about 50,000 parts per billion.

4. A process according to claim 1, wherein the mercury-containing hydrocarbon fluid feed is a liquid.

5. A process according to claim 4, wherein the mercury-containing hydrocarbon fluid feed includes at least one member of a group comprising:
   (i) a liquefied natural gas;
   (ii) a light distillate comprising liquid petroleum gas, gasoline, and/or naphtha;
   (iii) a natural gas condensate;
   (iv) a middle distillate comprising kerosene and/or diesel;
   (v) a heavy distillate; and
   (vi) a crude oil.

6. A process according to claim 1, wherein the mercury-containing hydrocarbon fluid feed is a gas.

7. A process according to claim 6, wherein the mercury-containing hydrocarbon fluid feed includes at least one member of a group comprising: natural gas and refinery gas.

8. A process according to claim 1, wherein [Cat$^+$] comprises a cationic species selected from the group consisting of:

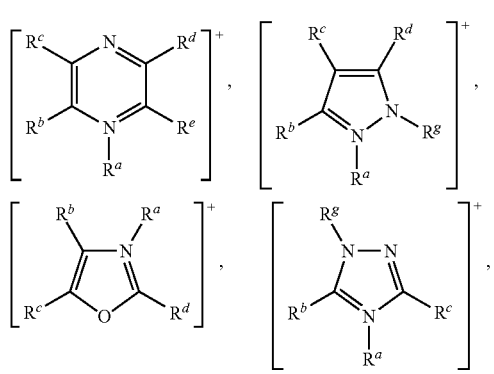

$R^a$, $R^b$, $R^c$, $R^d$, $R^e$, $R^f$ and $R^g$ are as defined in claim 1.

9. A process according to according to claim 8 wherein [Cat$^+$] comprises a cationic species selected from the group consisting of:

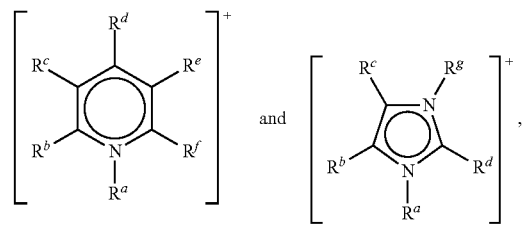

$R^a$, $R^b$, $R^c$, $R^d$, $R^e$, $R^f$, and $R^g$ are as defined in claim 1.

10. A process according to claim 9 wherein [Cat$^+$] comprises a cationic species selected from the group consisting of:

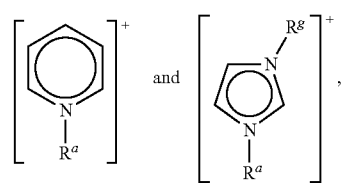

$R^a$ and $R^g$ are as defined in claim 1.

11. A process according to claim 10, wherein the cationic species is:

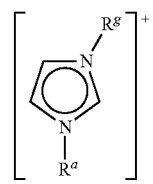

wherein: $R^a$ is selected from a $C_2$ to $C_{20}$, linear or branched alkyl group (such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl and n-octadecyl) and $R^g$ is selected from a $C_1$ to $C_5$, linear or branched alkyl group (such as methyl, ethyl, n-propyl, n-butyl and n-pentyl).

12. A process according to claim 1, wherein [Cat$^+$] comprises a cationic species selected from the group consisting of:

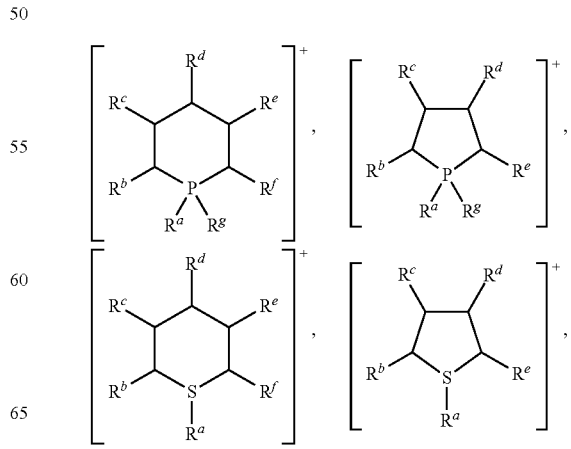

-continued

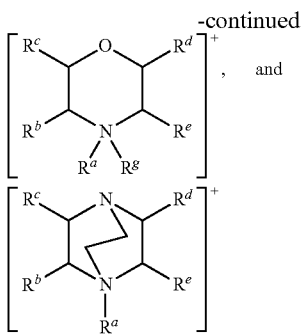

and $R^a$, $R^b$, $R^c$, $R^d$, $R^e$, $R^f$, and $R^g$ are as defined in claim 1.

13. A process according to claim 1, wherein [Cat⁺] is selected from the group consisting of:

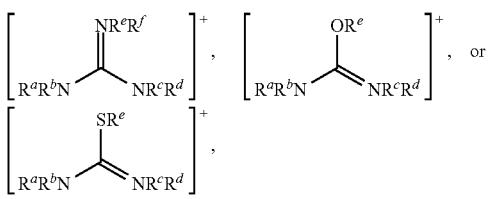

or $R^a$, $R^b$, $R^c$, $R^d$, $R^e$, and $R^f$ are as defined in claim 1.

14. A process according to claim 1, wherein [X⁻] comprises an anion selected from [I₃]⁻, [I₂Br]⁻, [IBr₂]⁻, [Br₃]⁻, [Br₂Cl]⁻, [BrCl₂]⁻, [ICl₂]⁻, [I₂Cl]⁻, and [Cl₃]⁻.

15. A process according to claim 14, wherein the anion is a perhalide selected from [I₃]⁻, [I₂Br]⁻, [IBr₂]⁻, [Br₃]⁻, [Br₂Cl]⁻, [BrCl₂]⁻, [ICl₂]⁻, [I₂Cl]⁻ and [Cl₃]⁻.

16. A process according to claim 1, wherein [X⁻] comprises an anion selected from [NO₃]⁻, [NO₂]⁻, [H₂PO₄]⁻, [HPO₄]²⁻, [PO₄]³⁻, [R₂OPO₃]²⁻, [(R²O)₂PO₂]⁻, [H₂PO₃]⁻, [HPO₃]²⁻, [R²OPO₂]²⁻, [(R²O)₂PO]⁻, [R¹PO₃]²⁻, [R¹P(O)(OR²)O]⁻, and [R²CO₂]⁻ wherein R¹ and R² are as defined in claim 1.

17. A process according to claim 1, wherein [X⁻] comprises an anion having an electron-rich sulfur or selenium moiety, said anion being selected from [NCS]⁻, [NCSe]⁻, [R²OCS₂]⁻, [R²₂NCS₂]⁻, [R¹CS₂]⁻, [(R²O)₂PS₂]⁻, [R¹S(O)₂S]⁻, [R²OS(O)₂S]⁻, wherein R¹ and R² are as defined in claim 1, and anions as defined in claim 1 comprising thiol, thioether, or disulfide substituents.

18. A process according to claim 1, wherein [X⁻] comprises an anion selected from [HSO₄]⁻, [SO₄]²⁻, [R²OSO₂O]⁻, [HSO₃]⁻, [SO₃]²⁻, [R²OSO₂]⁻, and [R¹SO₂O]⁻ wherein R¹ and R² are as defined in claim 1.

19. A process according to claim 1, wherein the ionic liquid is immobilised on an inert solid support.

20. A process according to claim 19, wherein the inert solid support is activated carbon.

21. A process according to claim 19, wherein the inert solid support is silica.

22. A process according to claim 1, wherein the ionic liquid is immiscible with the mercury-containing hydrocarbon fluid feed and the hydrocarbon fluid product.

23. A process according to claim 1, wherein the ionic liquid is contacted with the mercury-containing hydrocarbon fluid feed at a temperature of from −80° C. to 200° C.

24. A process according to claim 1, wherein the ionic liquid is contacted with the mercury-containing hydrocarbon fluid feed at atmospheric pressure.

25. A process according to claim 1, wherein the ionic liquid is in liquid form when contacted with the mercury-containing hydrocarbon fluid feed.

26. A process according to claim 1, wherein 1 to 10,000 moles of ionic liquid are contacted with the mercury-containing hydrocarbon fluid feed per mole of the mercury in the mercury-containing hydrocarbon fluid feed.

27. A process according to claim 1, wherein the hydrocarbon fluid product comprises 10% or less of the mercury content of the mercury-containing hydrocarbon feed.

28. A process according to claim 27, wherein the hydrocarbon fluid product comprises 5% or less of the mercury content of the mercury-containing hydrocarbon feed.

29. A process according to claim 28, wherein the hydrocarbon fluid product comprises 1% or less of the mercury content of the mercury-containing hydrocarbon feed.

30. A process according to claim 1, wherein the mercury-containing hydrocarbon feed and the ionic liquid are contacted by means of a continuous process or a batch process.

31. A process according to claim 30, wherein the mercury-containing hydrocarbon feed and the ionic liquid are contacted from about 1 minute to about 60 minutes.

32. A process according to claim 1, wherein the hydrocarbon:ionic liquid volume ratio is from 1000:1 to 10,000:1.

* * * * *